(12) United States Patent
Zhang et al.

(10) Patent No.: US 11,612,648 B2
(45) Date of Patent: Mar. 28, 2023

(54) METHOD FOR ADAPTING INFLUENZA VIRUSES TO VERO CELLS

(71) Applicant: YISHENG BIOPHARMA (SINGAPORE) PTE. LTD., Singapore (SG)

(72) Inventors: Yi Zhang, Singapore (SG); Yuhe Yan, Singapore (SG); Xu Zhang, Singapore (SG); Thomas Anthony Coton, Singapore (SG)

(73) Assignee: Yisheng Biopharma (Singapore) Pte Ltd, Singapore (SG)

( * ) Notice: Subject to any disclaimer, the term of this patent is extended or adjusted under 35 U.S.C. 154(b) by 284 days.

(21) Appl. No.: 16/960,283

(22) PCT Filed: Jan. 18, 2018

(86) PCT No.: PCT/SG2018/050030
§ 371 (c)(1),
(2) Date: Jul. 6, 2020

(87) PCT Pub. No.: WO2019/143291
PCT Pub. Date: Jul. 25, 2019

(65) Prior Publication Data
US 2021/0106672 A1 Apr. 15, 2021

(51) Int. Cl.
*A61K 39/12* (2006.01)
*C12N 7/00* (2006.01)
*A61K 39/00* (2006.01)
*C12N 5/00* (2006.01)
*A61K 39/145* (2006.01)

(52) U.S. Cl.
CPC .............. *A61K 39/145* (2013.01); *C12N 7/00* (2013.01); *C12N 2760/16152* (2013.01)

(58) Field of Classification Search
CPC .......... C12N 7/00; C12N 15/86; A61K 39/12; A61P 31/14; A61P 37/04
See application file for complete search history.

(56) References Cited

U.S. PATENT DOCUMENTS

2008/0187546 A1* 8/2008 Wasmoen ............... A61P 31/12
435/239

FOREIGN PATENT DOCUMENTS

WO      97/38094     10/1997

OTHER PUBLICATIONS

Hu et al., "A Vero-cell-adapted vaccine donor strain of Influenza A virus generated by serial passages", Vaccine, 30(2), 2014:374-381.*
Govorkova et al., (1995) "Replication of Influenza Viruses in a Green Monkey Kidney Continuous Cell Line (VERO)", Journal of Infectious Diseases. JID, 172(1):250-253, XP000983746.
Weibin et al., (2014) "A Vero-cell-adapted vaccine donor strain of influenza A virus generated by serial passages", Vaccine, Elsevier, 33(2):374-381, XP029117291.

* cited by examiner

*Primary Examiner* — Barry A Chestnut
(74) *Attorney, Agent, or Firm* — Bozicevic, Field & Francis LLP; Shweta Chandra

(57) ABSTRACT

A method for adapting an influenza virus to Vero cells is provided. The method comprises infecting Vero cells with the influenza virus, cultivating the infected Vero cells, harvesting influenza viruses of each passage, wherein infectious dose of the influenza viruses of one passage is greater than or equal to infectious dose of the influenza viruses of a previous passage. The present disclosure also relates to a composition. Said composition comprises polyriboinosinic acid-polyribocytidylic acid, at least one antibiotic or polyamide compound, at least one positive ion, influenza viruses and/or influenza antigens, wherein said influenza viruses and/or influenza antigens are acquired from Vero cell adapted influenza viruses.

19 Claims, 2 Drawing Sheets

METHOD FOR ADAPTING INFLUENZA VIRUSES TO VERO CELLS

TECHNICAL FIELD

This application relates to medical field, more particularly, to a method for adapting an influenza virus to Vero cells. Said method is used for producing a Vero cell adapted influenza virus. This application also relates to a composition, including a polyriboinosinic acid-polyribocytidylic acid (PIC), at least one antibiotic or polyamide compound, at least one positive ion, influenza viruses and/or influenza antigens, wherein said influenza viruses and/or influenza antigens are produced from the Vero cell adapted influenza virus.

BACKGROUND

Influenza virus infection, an important global respiratory infection, has resulted in considerable loss of life. Influenza viruses include influenza A viruses, influenza B viruses, influenza C viruses, and influenza D viruses. The influenza A viruses are main virulent pathogens for severe respiratory diseases and pandemic deaths. The epidemiological characteristics of influenza virus infection include rapid outbreak, quick spreading, with a broad host range, and easily infecting people in any age group. Therefore, there is a need to increase influenza vaccine production.

The Word Health Organization (WHO) or the Centers for Disease Control and Prevention (CDC) provides embryonated chicken egg-derived (ECE-derived) influenza virus seeds for influenza vaccine manufacture every year. So most influenza vaccines are produced in embryonated chicken eggs at present. This traditional method for vaccine production is time-consuming and costly. In addition, pathogens in the chicken eggs are prone to develop cross infection.

Hemagglutinin (HA), a major antigen of the influenza virus, exhibits high frequency of viral mutations and reassortment. The seasonal epidemic influenza viruses may be different from each other, which requires periodic replacement of the influenza virus seeds.

The influenza viruses used for vaccine production may be changed as WHO may replace the influenza virus seeds every year. It is difficult to produce enough seasonal vaccines using embryonated chicken eggs in a short time. Therefore, there are urgent public health tasks to resolve contradiction of vaccine supply and demand, and to develop vaccines that require minor dose of antigens and simpler administration ways to rapidly elicit strong immune responses.

Vero cell line is recommended by WHO as the only cell line for human vaccine production. The Vero cells have been used for human vaccine production for decades, and have been successfully used to develop vaccines for poliovirus and rabies virus. But the ECE-derived influenza viruses are not grown to high titer in the Vero cells. Prior arts do not provide a method for fast adapting of the ECE-derived influenza viruses to the Vero cells, more particularly, a method for adapting of the ECE-derived influenza viruses to the Vero cells in 5-10 passages. So it is urgent to develop a method for fast adapting of the influenza viruses to the Vero cells.

United States patent application US 20080187546 A1 provides a method for selecting an influenza virus for growth on tissue culture cells to produce a tissue culture adapted viral isolate. Said method includes serially diluting the influenza viruses into a multiplicity of influenza subpopulations, infecting the tissue culture cells by the influenza subpopulations, selecting the subpopulation with low multiplicity of infection (MOI) that produces cytopathic effects (CPE), harvesting the influenza viruses from the cells infected by the subpopulation with low MOI, infecting the tissue culture cells with the harvested influenza viruses, and repeating the process. Said method discloses the influenza viruses are serially diluted before each passage to obtain low MOI (less than 0.01), and infectious dose of the next passage is determined by observing the CPE. So it means there is a great deal of variability when determining the infectious dose of the next passage. Said method does not explore a method where the infectious dose of the next passage is greater than or equal to the infectious dose of this passage. Meanwhile, said method uses influenza viruses to contact monolayers of cells, which may only produce a small amount of influenza viruses (which is not available for large-scale production). Furthermore, the application does not disclose number of passages to obtain tissue culture cell adapted viruses, or disclose that said method could obtain the tissue culture cell adapted viruses in 5-10 passages. The whole contents of US 20080187546 A1 are incorporated herein by reference.

SUMMARY

According to one aspect of present disclosure, a method for adapting an influenza virus to Vero cells, wherein said method comprises:
infecting Vero cells with an influenza virus at a first infectious dose;
cultivating infected Vero cells in a spinner flask to produce viral activities;
harvesting a first influenza virus;
infecting Vero cells with said first influenza virus at a second infectious dose to produce viral activities, and harvesting a second influenza virus, wherein said second infectious dose is greater than or equal to said first infectious dose; and
repeating the process, and harvesting a Vero cell adapted influenza virus.

According to another aspect of present disclosure, a method for adapting influenza viruses to Vero cells, wherein said method comprises:
infecting Vero cells with an influenza virus at a first infectious dose;
cultivating infected Vero cells in a spinner flask to produce viral activities;
harvesting a first influenza virus;
infecting Vero cells with said first influenza virus at a second infectious dose to produce viral activities, and harvesting a second influenza virus; and
repeating the process, and harvesting a Vero cell adapted influenza virus, wherein at least one of said first infectious dose and said second infectious dose is expressed by MOI which ranges from 0.00001 to 2.0.

In some embodiments, said MOI may be 0.00001, 0.00005, 0.00010, 0.00050, 0.001, 0.005, 0.01, 0.05, 0.1, 0.5, 1.0, 1.5, or 2.0. In some particular embodiments, said MOI may be 0.00001, 0.00004, 0.00013, 0.0002, 0.0011, 0.0013, 0.002, 0.0022, 0.0026, 0.0072, 0.008, 0.018, 0.019, 0.030, 0.033, 0.05, 0.16, 0.22, 0.25, 0.47, 0.5, 0.63, 1.0, 1.58, 1.6, or 2.0.

In some embodiments, the first infectious dose may be 1%, 10%, 20%, 30%, 40%, 50%, 60%, 70%, 80%, 90%, or 100% of the second infectious dose.

The present disclosure further provides a method for producing influenza viruses. The method for producing influenza viruses may include a method for large-scale production of influenza virus infected cells. In some embodiments, the method for producing influenza viruses may include large-scale production of influenza virus infected cells by a single-use bioreactor.

The present disclosure further provides a vaccine, wherein said vaccine is produced from Vero cell adapted influenza viruses. In some embodiments, the vaccine may include inactivated viruses, attenuated viruses, and/or influenza antigens (e.g., hemagglutinin (HA), neuraminidase (NA), etc.).

The present disclosure further provides a composition, wherein said composition may include PIKA (a composition including a polyriboinosinic acid-polyribocytidylic acid (PIC), at least one antibiotic or polyamide compound, at least one positive ion), influenza viruses and/or influenza antigens, or any other components for implementing the composition. The influenza antigens include, but are not limited to, hemagglutinin (HA), neuraminidase (NA), or derivatives, or the like thereof. The polyamide compound may include spermidine sault, spermidine, N-(3-aminopropyl), N-(3-aminopropyl)-1,4-butandiamine, spermine BR, spermine, OS-dimethylphosphoramidothioate, polylysine, aminoglycoside, or any combination thereof. The positive ion may include calcium, cadmium, lithium, magnesium, cerium, cesium, chromium, cobalt, deuterium, gallium, iodine, iron, zinc, or any combination thereof. The composition may be used to manufacture nasal-spray vaccines or any other form of vaccines.

The methods, vaccines, and the composition of the present disclosure, provides several technical improvements than prior arts. For example, the present disclosure establishes a method for adapting ECE-derived influenza viruses to Vero cells. More particularly, the present disclosure establishes a method for adapting ECE-derived influenza viruses to Vero cells in 5-10 passages. For another example, the present disclosure provides a method for cultivating infected Vero cells in a spinner flask, which benefits large-scale production of influenza viruses. For another example, the composition of the present disclosure decreases amount of antigens and reduces costs. In some embodiments, the composition of the present disclosure may be administrated to a subject by nasal spray, which induces both systematic immune responses and mucosal immune responses, and resolves a problem that intramuscular vaccines cannot elicit adequate mucosal immune responses.

BRIEF DESCRIPTION OF THE DRAWINGS

The present disclosure is further described in terms of exemplary embodiments. Some of these exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
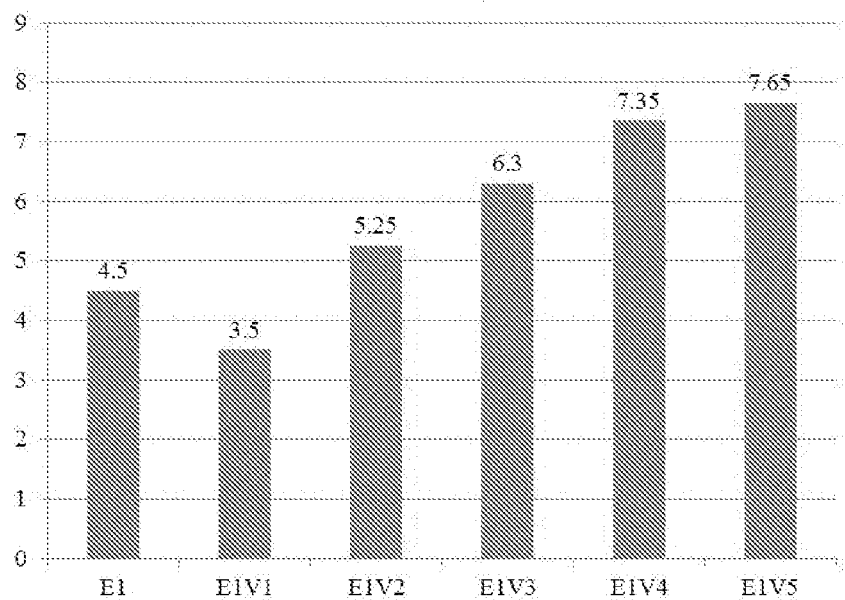
FIG. 1 illustrates results of (50% tissue culture infectious dose) $TCID_{50}$ assay of each passage of influenza virus A/California/7/2009(H1N1)pdm09 according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. Various modifications to the disclosed embodiments are also apparent to those skilled in the art, and general principles defined herein may be applied to other embodiments and applications without departing from the spirit and scope of the present disclosure.

It will be understood that unless defined otherwise, all technical and scientific terms used herein have the same meaning as commonly understood by those skilled in the art.

It will be understood that the singular forms "a", "and", and "the" include plural referents unless the context clearly dictates otherwise. As used herein, the term "and/or" includes any and all combinations of one or more of the associated listed items. It will be further understood that the terms "include", and/or "comprise", when used in this disclosure, specify the presence of elements, steps, operations, and/or components, but not exclude the presence or addition of one or more other elements, steps, operations, and/or components thereof.

The present disclosure provides a method for adapting an influenza virus to Vero cells, comprising:
  infecting Vero cells with an influenza virus at a first infectious dose;
  cultivating infected Vero cells in a spinner flask to produce viral activities;
  harvesting a first influenza virus;
  infecting Vero cells with said first influenza virus at a second infectious dose to produce viral activities, and harvesting a second influenza virus, wherein said second infectious dose is greater than or equal to said first infectious dose; and
  repeating the process, and harvesting a Vero cell adapted influenza virus.

According to another aspect of present disclosure, a method for adapting an influenza virus to Vero cells, wherein said method comprises:
  infecting Vero cells with an influenza virus at a first infectious dose;
  culturing infected Vero cells in a spinner flask to produce viral activities;
  harvesting a first influenza virus;
  infecting Vero cells with said first influenza virus at a second infectious dose to produce viral activities, and harvesting a second influenza virus; and
  repeating the process, and harvesting Vero cell adapted influenza viruses, wherein at least one of said first infectious dose and said second infectious dose is expressed by MOI which ranges from 0.00001 to 2.0.

In some embodiments, said MOI may be 0.00001, 0.00005, 0.00010, 0.00050, 0.001, 0.005, 0.01, 0.05, 0.1, 0.5, 1.0, 1.5, or 2.0. In some particular embodiments, said MOI may be 0.00001, 0.00004, 0.00013, 0.0002, 0.0011, 0.0013, 0.002, 0.0022, 0.0026, 0.0072, 0.008, 0.018, 0.019, 0.030, 0.033, 0.05, 0.16, 0.22, 0.25, 0.47, 0.5, 0.63, 1.0, 1.58, 1.6, or 2.0.

In some embodiments, the first infectious dose may be 1%, 10%, 20%, 30%, 40%, 50%, 60%, 70%, 80%, 90%, or 100% of the second infectious dose.

According to some embodiments of the present disclosure, the influenza virus may be acquired from a cell(s), a tissue(s) (e.g., a lung, etc.) and/or a subject(s) (e.g., a human subject, etc.). In some embodiments, the influenza virus may be acquired from embryonated chicken eggs (e.g., from allantoic cavity of chicken embryo, or from amniotic membrane of chicken embryo) and/or lungs, or any other cells, or tissues. In some embodiments, the influenza virus may be acquired from a throat swab, a nasal swab, and/or a third party (e.g., WHO, or CDC). The influenza virus may be identified by type, subtype, and/or location where the influenza virus is collected. In some embodiments, the influenza virus may be selected from influenza A viruses (e.g., H1N1, H1N2, H3N2, H3N8, H5N1, H7N7, H7N9, etc.), influenza B viruses, influenza C viruses, or the like viruses, or any combination thereof. Merely by way of example, the influenza virus may be A/California/7/2009(H1N1)pdm09, A/Michigan/45/2015(H1N1)pdm09, A/Switzerland/9715293/2013 (H3N2), A/Hong Kong/4801/2014(H3N2), B/Brisbane/60/2008, or B/Phuket/3073/2013, or any combination thereof.

According to some embodiments of the present disclosure, the first infectious dose and the second infectious dose refer to infectious doses of any two successive passages of the influenza viruses used to produce next passages of influenza viruses. For example, the first infectious dose may refer to an infectious dose of the ECE-derived influenza viruses used to produce a first passage of influenza viruses, and the second infectious dose may refer to an infectious dose of the first passage viruses used to produce a second passage. For another example, the first infectious dose may refer to an infectious dose of the first passage viruses used to produce the second passage, and the second infectious dose may refer to an infectious dose of the second passage viruses used to produce a third passage. For another example, the first infectious dose may refer to an infectious dose of the second passage viruses used to produce the third passage, and the second infectious dose may refer to an infectious dose of the third passage viruses used to produce a fourth passage. For another example, the first infectious dose may refer to an infectious dose of the third passage viruses used to produce the fourth passage, and the second infectious dose may refer to an infectious dose of the fourth passage viruses used to produce a fifth passage.

According to some embodiments of the present disclosure, a first infectious dose and/or a second infectious dose may be defined by a plurality of parameters. In some embodiments, the first infectious dose and/or the second infectious dose may be defined by volume of influenza viruses harvested in liquid form, $TCID_{50}$, MOI, or any other parameters. The term "harvest" used herein refers to at least one of the operations, including acquiring cells infected with influenza viruses, acquiring influenza viruses in contents of the infected cells, isolating/purifying the influenza viruses, and isolating/purifying influenza antigens. In some particular embodiments, the first infectious dose and/or the second infectious dose may be defined by MOI of influenza viruses used to infect cells. Merely by way of example, the first infectious dose and/or the second infectious dose may be expressed by MOI which may range from 0.00001 to 2.0. It should be noted that the first infectious dose and/or the second infectious dose may be determined according to number of passages, viral activities (e.g., HA titer, CPE, etc.) of one passage, number of Vero cells to be infected at each passage of influenza viruses, and/or any other parameters.

In some embodiments, the first infectious dose and the second infectious dose may be defined by MOI, which may be 0.00001, 0.00005, 0.00010, 0.00050, 0.001, 0.005, 0.01, 0.05, 0.1, 0.5, 1.0, 1.5, or 2.0. More particularly, the MOI may be 0.00001, 0.00004, 0.00013, 0.0002, 0.0011, 0.0013, 0.002, 0.0022, 0.0026, 0.0072, 0.008, 0.018, 0.019, 0.030, 0.033, 0.05, 0.16, 0.22, 0.25, 0.47, 0.5, 0.63, 1.0, 1.58, 1.6, or 2.0. In some embodiments of the present disclosure, the first infectious dose may be 1%, 10%, 20%, 30%, 40%, 50%, 60%, 70%, 80%, 90%, or 100% of the second infectious dose.

The viral activities of the present disclosure include, but are not limited to, viral replication, viral production, hemagglutinin (HA) titer or neuraminidase (NA) titer.

The terms "adapting" and "adapted" refer to performances and/or abilities that enable influenza viruses attaching and entering the host cells, replicating in the host cells, and/or completing viral assembly.

The present disclosure further provides a method for influenza virus production. The method for influenza virus production may include large-scale production of infected cells. In some embodiments, the method for influenza virus production may include use of a single-use bioreactor for large-scale cell culture.

The present disclosure further provides a vaccine. The vaccine of the present disclosure may be manufactured by Vero cell adapted influenza viruses. In some embodiments, the vaccine may include inactivated influenza viruses, attenuated influenza viruses, and/or influenza antigens (e.g., HA, NA, etc.).

The present disclosure further provides a composition. The composition of the present disclosure includes, but is not limited to, PIKA (a composition including PIC, at least one antibiotic or polyamine compound, at least one positive ion, etc.), influenza viruses and/or influenza antigens, and/or any other components for implementing the composition. The influenza antigens include, but are not limited to, HA, NA, derivatives of HA or NA, or the like. The positive ion may be selected from calcium, cadmium, lithium, magnesium, cerium, cesium, chromium, cobalt, deuterium, gallium, iodine, iron, zinc, or the combination thereof. The composition may be used to manufacture influenza vaccines for nasal spray or influenza vaccines utilizing any other methods of administration (e.g., intramuscular delivery, intravenous delivery, oral administration, etc.).

In the following detailed description, numerous specific details are set forth by way of examples in order to provide a thorough understanding of the relevant disclosure. It should be noted, to those skilled in the art, that the present disclosure may be practiced without such details. Various modifications or changes may be applied to the disclosed embodiments and other embodiments without departing the spirit and scope of the present disclosure.

EXAMPLES

Example 1: Vero Cell Cultivation

In some embodiments of the present disclosure, the continuous cell line used for influenza virus adaption is the Vero cell line. The Vero cells have been recommended by WHO for influenza vaccine production. More particularly, the Vero cell line is the only cell line recommended by WHO for manufacturing human influenza vaccines.

In some embodiments, passage number of the Vero cells is less than 160. In some more particular embodiments, the passage number of the Vero cells is 121.

It is known to those skilled in the art that numerous media may be used for Vero cell cultivation. In some embodiments, the Vero cells may be cultivated in Dulbecco's modified Eagle's medium (DMEM) containing fetal bovine serum. For example, the Vero cells may be cultivated in the DMEM containing 5% fetal bovine serum at 37° C.

The Vero cells may be cultivated in a plurality of containers. In some embodiments, the Vero cells may be cultivated in a spinner flask. The Vero cells may not only grow with attaching to the inner wall of the containers. For example, the Vero cells may attach to growth media suspending in the culture. The term "growth media" refers to media that utilize their physical characteristics (e.g., structure of holes), or their chemical characteristics (e.g., chemicals with cell affinity) to support cell growth. In some embodiments, the growth media may be sphere microcarriers (e.g., Cytodex 1).

It should be noted that, to those skilled in the art, the cells used for influenza virus adaption may not limit to the Vero cells. Numerous cells may be used for influenza virus adaption, including MDCK cells, PER.C6 cells, BHK-21, BSC, HEK, MDBK, BK21, and CV-1.

Example 2: Method of Acquiring Influenza Virus

According to some embodiments of the present disclosure, the influenza virus may be acquired from numerous sources. In some embodiments, the influenza virus may be acquired from a nasal swab(s), a throat swab(s), a live specimen(s), a dead specimen(s), or any other sources. In some embodiments, the influenza virus may be acquired from an infected subject, an organization (e.g., WHO, CDC, American Type Culture Collection (ATCC), etc.), and/or a laboratory. The infected subject may include an animal subject, or a human subject. For example, the influenza virus may be acquired from embryonated chicken eggs provided by WHO. The influenza virus may be acquired by any method of isolating and purifying the influenza viruses from the sources. Viral activities of the influenza virus may be determined by qualitative analysis, and/or quantitative analysis (e.g., HA titer, NA titer, viral production, etc.).

Example 3: Passage and Harvest

The Vero cells may be infected by the ECE-derived influenza viruses at an infectious dose. The infectious dose may be expressed by MOI of the influenza virus. In some embodiments, the infectious dose may range from 0.00004 to 0.5. In some particular embodiments, the infectious dose may be 0.00004, 0.0013, 0.0026, 0.008, 0.04, or 0.5. In some embodiments, two or more values of the infectious dose may be used in Vero cell infection. For example, two values of the infectious dose may be used, where one value may be 1%-100% (e.g., 10%, 25%, 50%, 75%, or 100%) of the other value.

The infected Vero cells may be cultivated in cell medium. In some embodiments, the infected Vero cells may be cultivated in VP medium at 34° C. In some embodiments, one or more substances may be added into cell culture. For example, glutamine may be added based on cell metabolism. The infected Vero cells may be cultivated for acquiring influenza viruses of the first passage. In some embodiments, time for harvesting the influenza viruses and/or value of the infectious dose of the ECE-derived influenza viruses may be determined by acquiring some parameters including cytopathic effects (CPEs), ability of cell attaching to the growth media or the container, and/or HA titer. The CPE refers to any effect generated by influenza virus infection, which includes but is not limited to, cell rounding, degeneration, detachment of cells from a support (e.g., growth media, a tissue culture dish, T-flask, etc.), or apoptosis. In some embodiments, the influenza viruses of the first passage may be acquired from the Vero cells which are infected by influenza viruses at one of two values of the infectious dose of the ECE-derived viruses.

The influenza viruses of the first passage may be used to infect Vero cells at an infectious dose of a first passage. The Vero cells may be further cultivated for acquiring influenza viruses of the second passage. In some embodiments, two or more values of the infectious dose of the first passage may be used to infect the Vero cells, and to acquire influenza viruses with high viral activities. Similarly, the influenza viruses of the second passage may be used to infect Vero cells at an infectious dose of a second passage, and the infected Vero cells may be further cultivated for acquiring influenza viruses of a third passage.

In some embodiments, the infectious dose of the first passage is less than, or equal to, the infectious dose of the second passage. In some embodiments, the infectious dose of the first passage is 1%-100% of the infectious dose of the second passage. In some particular embodiments, the infectious dose of the first passage is 1%, 10%, 20%, 30%, 40%, 50%, 60%, 70%, 80%, 90%, 100% of the infectious dose of the second passage.

Repeat the process for several passages. In some embodiments, the number of passages of the influenza viruses ranges from 5 to 10. In some particular embodiments, the number of passages of influenza viruses is 5, 6, 7, 8, 9, or 10.

Harvest the Vero cell adapted influenza viruses. The Vero cell adapted influenza viruses may be determined by one or more parameters. The parameters include but are not limited to number of passages, HA and $TCID_{50}$ titers, CPE, mutation of HA gene, or the combination thereof. In some embodiments, the Vero cell adapted influenza viruses may be determined by the number of passages. In some embodiments, the Vero cell adapted influenza viruses may be acquired when the number of passages ranges from 5 to 10 (e.g., the number of passages may be 5, 6, 7, 8, 9, or 10.). In some embodiments, the Vero cell adapted influenza viruses may be acquired when viral activities of a certain passage are greater than viral activities of the influenza virus acquired from the embryonated chicken eggs (e.g., increase of $TCID_{50}$ titer), and when the viral activities of a certain passage reach or are greater than an expectation value (e.g., HA titer reaches 32, 64, 128, 256, 512, or greater), or keep the same value for at least two consecutive passages (e.g., HA titer of one passage is 80%-120% of HA titer of the previous passage). For example, the Vero cell adapted influenza viruses may be acquired in a condition that $TCID_{50}$ titer of a certain passage are greater than those of the influenza virus acquired from the embryonated chicken eggs (e.g., from 4 $Log_{10}TCID_{50}$/ml increases to 5, 6, 7, 8 and even 9 $Log_{10}TCID_{50}$/ml, etc.), HA titer of a certain passage reaches or is greater than an expectation value (e.g., HA titer reaches 32, 64, 128, 256, 512, or greater), or HA titers keep the same value for at least two consecutive passages (e.g., HA titer of one passage is 80%-120% of HA titer of the previous passage), and CPE (e.g., 80%-100% of cells showing CPE). In some embodiments, the Vero cell adapted influenza viruses may be acquired in a condition that only minor (e.g., 1, 2, 3, etc.) non-synonymous mutation sites (such non-synonymous mutation sites are not located in or near cleavage site of HA gene) are identified in several passages (e.g., two successive passages, three successive passages, four successive passages, five successive passages, etc.).

Example 4: The Vero Cell Adapted Influenza Viruses

According to some embodiments of the present disclosure, the method for adapting the influenza viruses to the Vero cells may be applied to a plurality of influenza viruses. Table 1 illustrates infectious doses of each passage of exemplary influenza viruses according to some embodiments of the present disclosure.

TABLE 1

Infectious doses of passages

| Influenza virus | ECE-derived viruses used for producing E1V1 ($1^{st}$ dose) | E1V1 used for producing E1V2 ($2^{nd}$ dose) | E1V2 used for producing E1V3 ($3^{rd}$ dose) | E1V3 used for producing E1V4 ($4^{th}$ dose) | E1V4 used for producing E1V5 ($5^{th}$ dose) |
|---|---|---|---|---|---|
| A/California/7/2009(H1N1)pdm09 | 0.0013 | 0.00013 | 0.0072 | 0.030 | 0.22 |
| A/Michigan/45/2015(H1N1)pdm09 | 0.00004 | 0.018 | 0.019 | 1.58 | 1.0 |
| A/Switzerland/9715293/2013(H3N2) | 0.04 | 0.0011 | 0.033 | 1.6 | 0.5 |
| A/Hong Kong/4801/2014(H3N2) | 0.5 | 0.16 | 0.47 | 1.6 | 1.0 |
| B/Brisbane/60/2008 | 0.008 | 0.002 | 0.0022 | 0.05 | 0.5 |
| B/Phuket/3073/2013 | 0.0026 | 0.00004 | 0.0002 | 0.25 | 0.63 |

Note:
the infectious dose of each passage is expressed by MOI.

According to Table 1, six exemplary influenza viruses are used to generate the Vero cell adapted influenza viruses. The Vero cell adapted influenza viruses are acquired with a number of passages less than or equal to 5. According to Table 1, values of the infectious dose of the first passage, the infectious dose of the second passage, and the infectious dose of the third passage or the infectious dose of the fourth passage keep increasing. Particularly, for A/California/7/2009(H1N1)pdm09, B/Phuket/3073/2013 and B/Brisbane/60/2008, values of the infectious dose of the first passage, the infectious dose of the second passage, the infectious dose of the third passage, and the infectious dose of the fourth passage keep increasing. For influenza viruses A/Michigan/45/2015(H1N1)pdm09, A/Switzerland/9715293/2013 (H3N2), and A/Hong Kong/4801/2014(H3N2), values of the infectious dose of the first passage, the infectious dose of the second passage, and the infectious dose of the third passage keep increasing.

Example 5: A/California/7/2009(H1N1)Pdm09 Adapting to the Vero Cells

A/California/7/2009(H1N1)pdm09 is an influenza A virus recommended by WHO in year of 2010-2017 as a strain for producing influenza vaccine used in the Northern Hemisphere. Original A/California/7/2009(H1N1)pdm09 viruses (named as E1 viruses) acquired from CDC are adapted to the embryonated chicken eggs, and show a low $TCID_{50}$ value (only 4.5 $Log_{10}TCID_{50}$/ml) when cultivated in the Vero cells. The method of the present disclosure is applied to the A/California/7/2009(H1N1)pdm09 viruses for acquiring Vero cell adapted viruses. After being passed in the Vero cells over 5 passages, the A/California/7/2009(H1N1) pdm09 viruses are adapted to the Vero cells and can be used for large-scale production in a bioreactor, with increased value of $TCID_{50}$ titer (from 4.5 $Log_{10}TCID_{50}$/ml to 7.65 $Log_{10}TCID_{50}$/ml) and increased value of HA titer (from 4 or 8 to 32 or 64).

In some embodiments, the method for adapting the A/California/7/2009(H1N1)pdm09 viruses to the Vero cells is carried out as follows:

Add 15 ml of sterilized microcarrier Cytodex 1 (2%, w/v) into two 100 ml spinner flasks, respectively. Wash the Cytodex 1 once by 25 ml of 5% FBS-DMEM (i.e., DMEM containing 5% fetal bovine serum), and let the medium stand for 5-10 minutes. Remove supernatant carefully, add 5% FBS-DMEM medium to a total volume of 40 ml, place the spinner flasks on the magnetic stirrer in a $CO_2$ incubator, incubate the microcarrier at 37° C., 5% $CO_2$ and 30 rpm for 1 hour or overnight.

The Vero cells are cultivated in a T-300 flask(s) to form monolayers. The Vero cells are trypsinized, and transferred into the spinner flasks containing the microcarrier. Seeding density of the Vero cells is $2.5 \times 10^5$/ml, add 5% FBS-DMEM to a total volume of 100 ml. Place the spinner flasks on the magnetic stirrer in the $CO_2$ incubator, and cultivate the Vero cells at 37° C., 5% $CO_2$ and 30 rpm. When the Vero cells become confluent on the microcarrier, the density of the Vero cells is about $1 \times 10^6$/ml. Take out the spinner flasks, and let them stand for 5 minutes. Remove the supernatant carefully, wash the microcarrier twice with PBS (80 ml×2), once with VP medium (50 ml x1), add 30 ml VP medium (the total volume should be about 40 ml), and add trypsin to a final concentration of 20 μg/ml.

Use two different infectious doses (expressed by MOI: 0.00065 and 0.0013) to infect the Vero cells. The two spinner flasks are placed on the magnetic stirrer in a $CO_2$ incubator. The infected Vero cells are cultivated at 34° C., 5% $CO_2$ and 30 rpm. After the infected Vero cells are cultivated for 1-2 hours or overnight, add the VP medium containing the trypsin (20 μg/ml) to a total volume of 100 ml, and cultivate the Vero cells at 34° C., 5% $CO_2$ and 30 rpm. Observe CPE with microscope and detect HA titer daily. Add 5-10 μg/ml trypsin on the day 3 after infection. Add glutamine (1 mM) if necessary based on the cell metabolism. About 80%-100% of the Vero cells show the CPE (e.g., cell rounding, detaching from the microcarrier) on day 5 after infection. Choose the spinner flask in which the Vero cells show more severe CPE and higher HA titer in the culture, transfer the culture and the microcarrier to a 50 ml sterilized centrifuge tube, centrifuge at 1000 rpm for 5 minutes, take out supernatant carefully. Harvested influenza viruses are named as E1V1 viruses. Detect titers of $TCID_{50}$ and HA and store in −80° C.

The E1V1 viruses are further passed to a next passage (named as E1V2 viruses) according to the same methods of cell culture, medium replacement, and virus infection except that the infectious dose of the viruses may be different. The infectious doses (expressed by MOI) of E1V1 viruses for producing the E1V2 viruses in the spinner flasks are 0.000065 and 0.00013, respectively. Similarly, the infectious doses (expressed by MOI) of the E1V2 viruses for producing E1V3 viruses are 0.0037 and 0.0072, the infectious doses (expressed by MOI) of the E1V3 viruses for producing E1V4 viruses are 0.015 and 0.03, and the infectious doses (expressed by MOI) of the E1V4 viruses for producing E1V5 viruses are 0.11 and 0.22.

Figure 3:
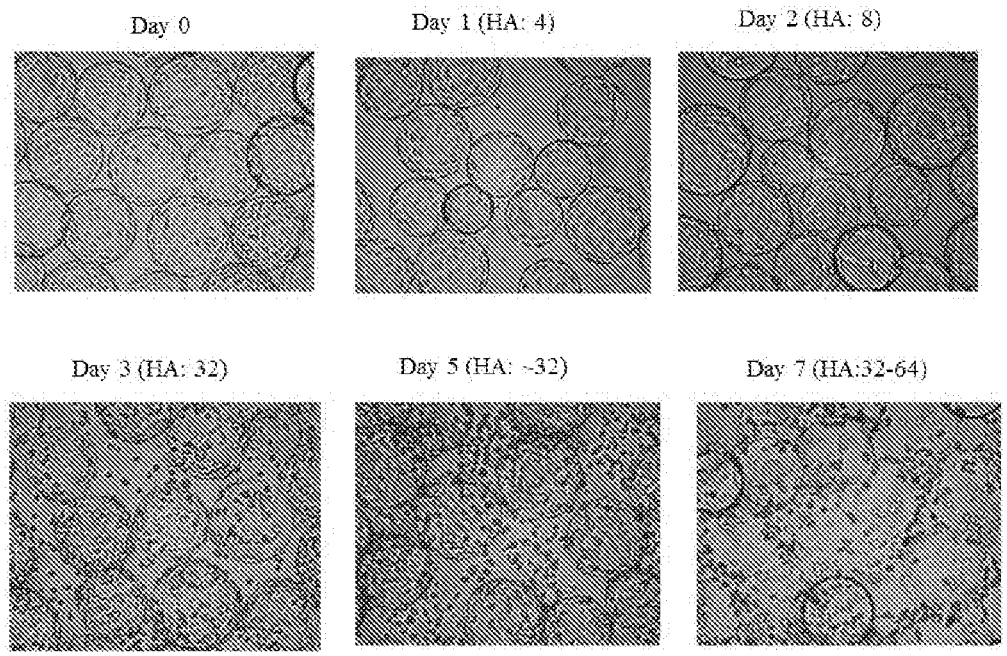
FIG. 3 illustrates CPE of Vero cells infected with E1V5 viruses of A/California/7/2009(H1N1)pdm09 according to some embodiments of the present disclosure.

Sequence analysis shows that HA gene of the E1V5 viruses has only one non-synonymous mutation site (said non-synonymous mutation site is not located in or near the cleavage site of HA gene) compared to the influenza viruses acquired from embryonated chicken eggs. This mutation does not affect basic characteristics (e.g., ability to elicit immune responses) of HA antigen. FIG. 1 shows $TCID_{50}$ titer of each passage of A/California/7/2009(H1N1)pdm09. FIG. 3 shows cytopathic effects (CPEs) of the cells infected with the E1V5 viruses of A/California/7/2009(H1N1) pdm09. As illustrated in FIG. 3, after the infection day (the day the E1V4 viruses are used to infect the Vero cells), HA titer increases along with CPE becoming more severe during the infectious period.

Example 6: B/Brisbane/60/2008 Adapting to the Vero Cells

B/Brisbane/60/2008 is an influenza B virus recommended by WHO as a strain for producing influenza vaccine used in the Northern Hemisphere. The B/Brisbane/60/2008 viruses acquired from the embryonated chicken eggs show a low $TCID_{50}$ titer (only 5.6 $Log_{10}TCID_{50}$/ml) when cultivated in the Vero cells. The method of the present disclosure is applied to the B/Brisbane/60/2008 viruses for acquiring Vero cell adapted viruses. After being passed in the Vero cells over 5 passages, the B/Brisbane/60/2008 viruses are adapted to the Vero cells and can be used for large-scale production in a bioreactor, with increased value of $TCID_{50}$ titer (about 8.1 $Log_{10}TCID_{50}$/ml) and increased value of HA titer (about 64 or higher).

In some embodiments, the method for adapting the B/Brisbane/60/2008 viruses to the Vero cells is carried out as follows:

The original B/Brisbane/60/2008 viruses (named as E1 viruses) acquired from embryonated chicken eggs are used to infect the Vero cells in two spinner flasks. The infectious doses of the original B/Brisbane/60/2008 viruses for the spinner flasks are 0.004 and 0.008, respectively. The two spinner flasks are placed on the magnetic stirrer in the $CO_2$ incubator. The Vero cells are cultivated at 34° C., 5% $CO_2$ and 30 rpm. After the Vero cells are cultivated for 1-2 hours or overnight, add the VP medium containing the trypsin (20 μg/ml) to a total volume of 100 ml, and cultivate the Vero cells at 34° C., 5% $CO_2$ and 30 rpm. Observe CPE and detect HA titer daily after infection. Add 5-10 μg/ml trypsin on day 3 after infection. Add glutamine (1 mM) if necessary based on the cell metabolism. About 80%-100% of the Vero cells show the CPE (e.g., cell rounding, detaching from the microcarrier) on day 5 after infection. Choose the spinner flask in which the Vero cells show more severe CPE and higher HA titer in the culture, transfer the culture and the microcarrier to a 50 ml sterilized centrifuge tube, centrifuge at 1000 rpm for 5 minutes, take out supernatant carefully. The harvested influenza viruses are named as E1V1 viruses. Detect titers of $TCID_{50}$ and HA and store in −80° C. The E1V1 viruses are further passed to a next passage (named as E1V2 viruses) according to the same methods of cell culture, medium replacement, and virus infection except that the infectious doses of the viruses may be different. The infectious doses (expressed by MOI) of the E1V1 viruses for producing the E1V2 viruses are 0.001 and 0.002. Similarly, the infectious doses (expressed by MOI) of the E1V2 viruses for producing E1V3 viruses are 0.0011 and 0.0022, the infectious doses (expressed by MOI) of the E1V3 viruses for producing E1V4 viruses are 0.05 and 0.10, the infectious doses (expressed by MOI) of the E1V4 viruses for producing E1V5 viruses are 0.5 and 1.0.

Figure 2:
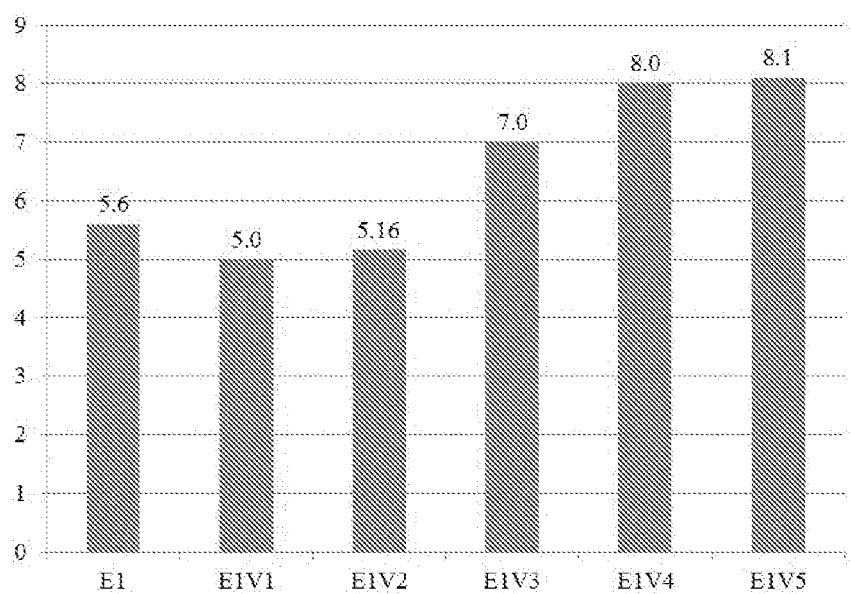
FIG. 2 illustrates results of $TCID_{50}$ assay of each passage of influenza virus B/Brisbane/60/2008 according to some embodiments of the present disclosure.
Figure 4:
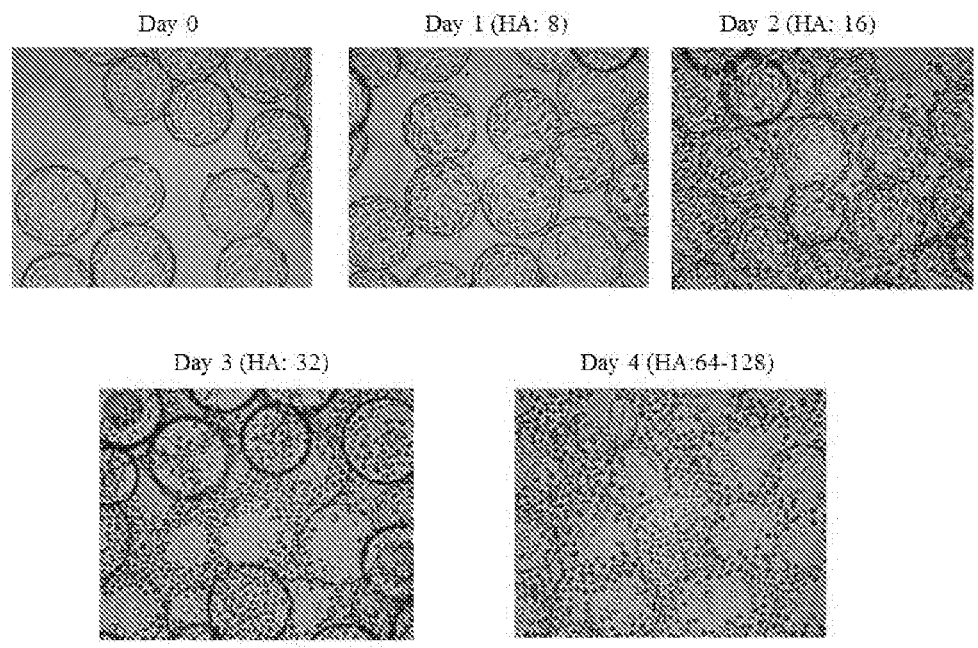
FIG. 4 illustrates CPE of Vero cells infected with E1V5 viruses of B/Brisbane/60/2008 according to some embodiments of the present disclosure.

Sequence analysis shows that HA gene of the E1V5 viruses has only two non-synonymous mutation sites (said non-synonymous mutation sites are not located in or near cleavage site of HA gene) compared to the influenza viruses acquired from embryonated chicken eggs. These mutations do not affect basic characteristics of HA antigen. FIG. 2 shows $TCID_{50}$ titer of each passage of B/Brisbane/60/2008. FIG. 4 shows cytopathic effects (CPEs) of cells infected with the E1V5 viruses of B/Brisbane/60/2008. As illustrated in FIG. 4, after the infection day (the day the E1V4 viruses are used to infect the Vero cells), HA titer increases along with CPE becoming more severe during the infectious period.

While the present disclosure has been described with reference to particular embodiments, it will be understood that the embodiments are illustrative and that the scope is not limited. Alternative embodiments of the present disclosure will become apparent to those having ordinary skill in the art to which the present disclosure pertains. Such alternative embodiments are considered to be encompassed within the spirit and scope of the present disclosure.

What is claimed is:

1. A method for adapting an influenza virus to Vero cells, comprising:
   infecting Vero cells with an influenza virus at a first infectious dose;
   cultivating infected Vero cells in a spinner flask to produce viral activities;
   harvesting a first influenza virus;
   infecting Vero cells with said first influenza virus at a second infectious dose to produce viral activities, wherein said second infectious dose is greater than or equal to said first infectious dose;
   harvesting a second influenza virus; and
   repeating the process, and harvesting a Vero cell adapted influenza virus.

2. A method of claim 1, wherein at least one of said first infectious dose and said second infectious dose is expressed by MOI, and the MOI is 0.00001, 0.00005, 0.0001, 0.0005, 0.001, 0.005, 0.01, 0.05, 0.1, 0.5, 1.0, 1.5, 2.0, or any value between 0.00001 and 2.0.

3. A method of claim 1, wherein at least one of said first infectious dose and said second infectious dose is expressed by MOI, and the MOI of influenza virus is 0.00001, 0.00004, 0.00013, 0.0002, 0.0011, 0.0013, 0.002 0.0022, 0.0026, 0.0072, 0.008, 0.018, 0.019, 0.030, 0.033, 0.05, 0.16, 0.22, 0.25, 0.47, 0.5, 0.63, 1.0, 1.58, 1.6, or 2.0.

4. A method of claim 3, wherein said first infectious dose is 1%, 10%, 20%, 30%, 40%, 50%, 60%, 70%, 80%, 90%, or 100% of said second infectious dose.

5. A method of claim 1, wherein said viral activities comprise viral replication, viral production, hemagglutinin (HA) titer or neuraminidase (NA) titer.

6. A method of claim 1, further comprising passing an influenza virus in the Vero cells with a number of passages of 5-10.

7. A method of claim 6, wherein said influenza virus is acquired from embryonated chicken eggs, allantoic cavity of chicken embryo, or amniotic membrane of chicken embryo.

8. A method of claim 7, wherein said influenza virus is selected from a group including A/California/7/2009(H1N1)pdm09, A/Michigan/45/2015(H1N1)pdm09, A/Switzerland/9715293/2013(H3N2), A/Hong Kong/4801/2014(H3N2), B/Brisbane/60/2008, and B/Phuket/3073/2013.

9. A method of claim 7, comprising using said Vero cell adapted influenza viruses to produce a composition, wherein said composition comprises polyriboinosinic acid-polyribocytidylic acid (PIC), at least one antibiotic or polyamide compound, at least one positive ion, influenza viruses and/or influenza antigens.

10. A method of claim 9, wherein at least one of said influenza antigens is selected from a group including HA and NA; wherein said polyamide compound is selected from a group including spermidine sault, spermidine, N-(3-aminopropyl), N-(3-aminopropyl)-1,4-butandiamine, spermine BR, spermine, OS-dimethylphosphoramidothioate, polylysine, and aminoglycoside; and wherein said positive ion is selected from a group including calcium, cadmium, lithium, magnesium, cerium, cesium, chromium, cobalt, deuterium, gallium, iodine, iron, and zinc.

11. A method of claim 9, comprising administrating said composition by nasal spray, intramuscular delivery, intravenous delivery, and/or oral administration.

12. A method of claim 1, comprising cultivating the Vero cells in a single-use bioreactor.

13. A method of claim 2, wherein at least one of said first infectious dose and said second infectious dose is expressed by MOI, and the MOI of influenza virus is 0.00001, 0.00004, 0.00013, 0.0002, 0.0011, 0.0013, 0.002 0.0022, 0.0026, 0.0072, 0.008, 0.018, 0.019, 0.030, 0.033, 0.05, 0.16, 0.22, 0.25, 0.47, 0.5, 0.63, 1.0, 1.58, 1.6, or 2.0.

14. A method of claim 2, wherein said viral activities comprise viral replication, viral production, hemagglutinin (HA) titer or neuraminidase (NA) titer.

15. A method of claim 2, further comprising passing an influenza virus in the Vero cells with a number of passages of 5-10.

16. A method of claim 10, comprising administering said composition by nasal spray, intramuscular delivery, intravenous delivery, and/or oral administration.

17. A method comprising:
infecting Vero cells with an influenza virus at a first infectious dose;
cultivating infected Vero cells in a spinner flask to produce viral activities;
harvesting a first influenza virus;
infecting Vero cells with said first influenza virus at a second infectious dose to produce viral activities, wherein said second infectious dose is greater than or equal to said first infectious dose;
harvesting a second influenza virus;
repeating the process, and harvesting a Vero cell adapted influenza virus,
wherein the steps of harvesting and infecting are both performed 5-10 times; and
using said Vero cell adapted influenza viruses to produce a composition, wherein said composition comprises polyriboinosinic acid-polyribocytidylic acid (PIC), at least one antibiotic or polyamide compound, at least one positive ion, influenza viruses and/or influenza antigens.

18. The method of claim 17, wherein said influenza virus is selected from a group including A/California/7/2009 (H1N1)pdm09, A/Michigan/45/2015(H1N1)pdm09, A/Switzerland/9715293/2013(H3N2), A/Hong Kong/4801/2014(H3N2), B/Brisbane/60/2008, and B/Phuket/3073/2013.

19. The method of claim 17, wherein at least one of said influenza antigens is selected from a group including HA and NA; wherein said polyamide compound is selected from a group including spermidine sault, spermidine, N-(3-aminopropyl), N-(3-aminopropyl)-1,4-butandiamine, spermine BR, spermine, OS-dimethylphosphoramidothioate, polylysine, and aminoglycoside; and wherein said positive ion is selected from a group including calcium, cadmium, lithium, magnesium, cerium, cesium, chromium, cobalt, deuterium, gallium, iodine, iron, and zinc.

* * * * *